(12) United States Patent
Froigneux et al.

(10) Patent No.: US 9,036,145 B2
(45) Date of Patent: May 19, 2015

(54) CONOSCOPIC ILLUMINATION OPTICAL DEVICE WITH A HOLLOW CONE FOR AN OPTICAL MICROSCOPE AND METHOD OF OPTICAL MICROSCOPY IN CONOSCOPY

(75) Inventors: Emmanuel Froigneux, Villeuneuve D'ascq (FR); Joachim Schreiber, Villeuneuve D'ascq (FR)

(73) Assignee: HORIBA JOBIN YVON SAS, Longjumeau (FR)

( * ) Notice: Subject to any disclaimer, the term of this patent is extended or adjusted under 35 U.S.C. 154(b) by 0 days.

(21) Appl. No.: 14/234,153

(22) PCT Filed: Jul. 20, 2012

(86) PCT No.: PCT/FR2012/051730
§ 371 (c)(1),
(2), (4) Date: Mar. 19, 2014

(87) PCT Pub. No.: WO2013/014379
PCT Pub. Date: Jan. 31, 2013

(65) Prior Publication Data
US 2014/0192355 A1 Jul. 10, 2014

(30) Foreign Application Priority Data

Jul. 22, 2011 (FR) ..................................... 11 56687

(51) Int. Cl.
*G01J 3/44* (2006.01)
*G02B 21/10* (2006.01)
*G01N 21/21* (2006.01)
(Continued)

(52) U.S. Cl.
CPC .............. *G02B 21/10* (2013.01); *G01N 21/211* (2013.01); *G02B 5/001* (2013.01); *G01N 21/65* (2013.01); *G02B 21/084* (2013.01); *G01N 21/658* (2013.01); *G02B 21/16* (2013.01); *G01N 2021/213* (2013.01); *G01J 3/10* (2013.01); *G01J 3/44* (2013.01); *G01J 3/0208* (2013.01); *G01J 3/0224* (2013.01); *G01J 3/0256* (2013.01); *G01J 4/00* (2013.01)

(58) Field of Classification Search
USPC .................................................. 356/300–334
See application file for complete search history.

(56) References Cited

U.S. PATENT DOCUMENTS

| 4,255,021 A | 3/1981 | Brunsden |
| 5,757,470 A | 5/1998 | Dewa et al. |
| 2007/0154938 A1* | 7/2007 | Oshida et al. ..................... 435/6 |

FOREIGN PATENT DOCUMENTS

| EP | 0 627 643 A2 | 12/1994 |
| WO | 2008/107702 A1 | 9/2008 |

OTHER PUBLICATIONS

International Search Report, dated Oct. 18, 2012, from corresponding PCT application.

*Primary Examiner* — Abdullahi Nur
(74) *Attorney, Agent, or Firm* — Young & Thompson

(57) ABSTRACT

A method of microscopy and an illumination optical device with a hollow cone for a microscope, the illumination device includes a first conical lens (1) able to receive a collimated incident light beam (10) and form a conical light beam (20), a second conical lens (5) arranged in such a way as to receive the conical light beam (20, 40) and to form a cylindrical light beam with a black background (50) and an optical lens (6) having an image focal plane (12) arranged in such a way as to receive the cylindrical light beam with a black background (50), to form a hollow cone light beam (60) and to focus the hollow cone light beam (60) into a point (18) in the image focal plane (12).

17 Claims, 8 Drawing Sheets

(51) Int. Cl.
*G02B 5/00* (2006.01)
*G01N 21/65* (2006.01)
*G02B 21/08* (2006.01)
*G02B 21/16* (2006.01)
*G01J 3/10* (2006.01)
*G01J 3/02* (2006.01)
*G01J 4/00* (2006.01)

CONOSCOPIC ILLUMINATION OPTICAL DEVICE WITH A HOLLOW CONE FOR AN OPTICAL MICROSCOPE AND METHOD OF OPTICAL MICROSCOPY IN CONOSCOPY

The present invention relates to a hollow-cone and point-focusing conoscopic illumination or lighting device for an optical microscope and a method of optical microscopy in conoscopy. This lighting device is particularly suitable for laser excitation of one point on a sample in a Raman microscope, in a photoluminescence or fluorescence microscope, or for a molecular micro-spectroscopy apparatus in back-scattering configuration. The lighting device also applies to a microellipsometer having a micrometric spatial resolution.

Optical microscopy is based on the use of imagery techniques whose performance is defined both by the lateral resolution, also called image resolution, and by the axial or depth of field resolution. The image resolution depends on the magnification of the optical imagery system, on the characteristics of the beam and on the quality of the optical components. The axial resolution is function not only of the optical characteristics of the imagery system but also of the properties of the sample to be analysed. The combination of the lateral resolution and the axial resolution determines the volume of analysis.

Various imagery techniques have been developed to improve the lateral and/or axial resolution of the microscopes. In particular, in a confocal microscope, a diaphragm is placed in the conjugated plane of the object so as to block the rays coming from points located outside the focal plane of the microscope objective. A confocal microscope thus allows improving the axial resolution. On the other hand, different lighting and imagery techniques have been developed so as to improve the contrast of the images: bright-field microscopy, dark-field microscopy, interferential microscopy, phase-contrast microscopy... In a bright-field microscope, a light beam illuminates the whole surface of the object to be analysed. The light beam transmitted or reflected by the object is collected to form a bright-field image of the object. Now, a bright-field lighting lights not only a plane of the object, but also a whole volume inside the incident cone of light, so that the axial resolution is low. The signal collected may come from the whole volume of the sample or from the substrate that supports the sample, for example a glass slide. In the case of small-thickness samples, such as a biological sample of a few micrometers of thickness, the intensity of the signal coming from the glass support may be higher than the intensity of the useful signal coming from the object to be analysed, which reduces the signal-to-noise ratio.

Dark-field microscopy is based on the use of a lighting beam whose central part is masked by a mask so as to generate a dark-centre light cone, the image of the source extending over the whole surface of the object to be analysed. Dark-field microscopy allows minimizing the transmitted quantity of light and collecting only the light that is scattered by the sample. Dark-field microscopy does not allow improving the axial resolution but allows highlighting small scattering elements that are not visible on a bright background. However, dark-field microscopy strongly reduces the collected light intensity and remains limited in lateral resolution.

Microspectrometry consists in coupling an optical microscope and a spectrometric analysis device, as for example Raman microspectrometry or photoluminescence or PL microspectrometry, fluorescence microspectrometry or microellipsometry. The various techniques of spectrometry generally use a lighting beam directed toward the sample to be analysed and collect an optical beam that is scattered (for Raman), reflected and/or transmitted (in ellipsometry). The excitation beam may be a laser beam, for example in Raman spectrometry or in monochromatic ellipsometry.

In a conventional configuration of Raman (or PL or fluorescence) microspectrometry, the sample is lighted in bright field by a laser beam focused by the microscope objective and the signal back-scattered about the optical axis is collected. An excitation laser beam may be focused so as to obtain an analysis with a micrometric lateral resolution. However, the in-depth spatial resolution (in the direction of the axis of the laser beam) hardly reaches the micrometric domain. Indeed, a laser beam generates a non-negligible optical radiation outside the focal point (or waist) of the laser beam. It is difficult to eliminate the spurious signals (for example, of fluorescence) coming from areas of the sample located outside the focusing plane, in particular in the case of a very-thin-layer sample deposited on a glass slide. It is known to couple a Raman spectrometer to a confocal microscope to improve the axial resolution.

The publication of M. V. Schulmerich et al., "Dark field Raman microscopy", Anal. Chem. 2010, 82, 6273-6280 describes a dark-field confocal Raman microscope comprising a lighting system provided with a mask centred on the axis of an incident laser beam, an optical system for collecting the Raman back-scattering signal coming from a sample and a dichroic slide to split the excitation laser beam and the Raman scattering beam. The lighting device forms a ring lighting area, which is focused at one point on the sample by an objective. Therefore, the laser illumination light beam comprises a dark axial cone and a luminous area comprised between the dark cone and a second coaxial cone. According to the publication of M. V. Shulmerich et al., the dark-field laser lighting allows increasing the signal-to-noise ratio of a Raman scattering coming from the surface of a sample by reducing the contribution of the background, which allows improving the measurement of very thin samples. However, the dark-field lighting device of Schulmerich et al. eliminates the major part of the energy of the incident laser beam.

On the other hand, to extract the Raman signal, which is low intensity compared to the reflection or the Rayleigh scattering, one or several injection/rejection filters (or notch filters) are generally used. An injection/rejection filter lets the incident beam pass through at the laser wavelength and angularly splits on the one hand the Rayleigh back-scattering beam at the incident wavelength and on the other hand the Raman back-scattering beam, offset in wavelength with respect to the wavelength of the laser beam. To extract so-called "low frequency" Raman measurements, i.e. at wavelengths close to the laser wavelength, it was up to now required to use filters with a high rejection rate and having a small spectral bandwidth about the laser wavelength. Such filters require a precise angular adjustment and are still very expensive.

Microellipsometry is another technique of microspectrometry in which the properties of a sample lighted by a polarized light are measured. Today, microellipsometry is limited in terms of axial and lateral resolution. Indeed, an ellipsometer generally has an optical sensitivity for a high incidence angle, comprised between 60 and 75 degrees relative to the normal to the sample surface. A microellipsometry apparatus generally uses a focusing objective inclined on the incident beam and a collecting objective inclined on the reflected beam. Due to the space required for the objectives under a high incidence angle, it is difficult to approach a microellipsometer close to the sample surface, and the incidence angle produces an oval focusing point on the surface (hence a broadening), which limits the lateral and axial resolution of a microellipsometer.

It is therefore desirable to improve the lateral and axial resolution of a microellipsometer, while keeping or improving the intensity of the ellipsometry signal.

Generally, it is desirable to improve the signal-to-noise ratio in microspectrometry to allow the analysis of small size and/or low thickness samples, such as thin biochemical samples or thin semi-conductor layers. More particularly, it is desirable to improve the axial and lateral resolution in Raman (or PL and/or fluo) microspectrometry or in microellipsometry. The use of a confocal and/or a dark field microscope may, in principle, allow improving the axial resolution. However, the occultation of the central part of the lighting beam reduces considerably the intensity of the excitation beam and reduces proportionally the intensity of the collected signal, whether it is a Raman diffusion signal or an ellipsometry signal. Now, Raman scattering signals are by nature of very low intensity. The use of a dark field in Raman microscopy is thus generally unfavourable, except in the case where the background, for example the substrate, generates a fluorescence signal far more important than the Raman signal of the sample to be analysed. Likewise, it is not desirable to reduce the intensity of ellipsometric signals.

One of the objects of the invention is to propose a device able to generate an illumination optical beam point-focused on a micrometric-size area of a sample, said illumination optical beam being intense enough to generate a scattering, reflection and/or transmission optical signal.

Another object of the invention is to propose a Raman microspectrometry or photoluminescence microspectrometry or fluorescence microspectrometry device.

Still another object of the invention is to propose a microellipsometry device.

Another object of the invention is to propose a microspectrometry method having a micrometric lateral resolution and an increased signal-to-noise ratio with respect to the methods of the prior art.

The present invention has for object to remedy the above-mentioned drawbacks and relates more particularly to a hollow-cone and point-focusing conoscopic illumination optical device for an optical microscope, comprising:
  illumination means comprising a point light source, said illumination means being able to generate a collimated incident light beam,
  an optical objective having an optical axis and an image focal plane, the optical objective being arranged so as to receive a cylindrical incident light beam and to form an image of the source at one point in the image focal point.
According to the invention, the illumination optical device comprises:
  an optical system comprising a first conical lens and a second conical lens, said optical system being arranged on the optical path of the incident light beam between the illumination means and the optical objective,
  the first conical lens being arranged so as to receive said collimated incident light beam and to form a first hollow-cone light beam having, in a plane transverse to the beam axis, a light distribution comprising a dark central part and a bright ring part,
  the second conical lens being arranged so as to receive said first hollow-cone light beam and to form a black-background cylindrical light beam having, in a plane transverse to the beam axis, a light distribution comprising a dark central part and a bright ring part, and
  in that the optical objective is arranged so as to receive said black-background cylindrical light beam and to form a second hollow-cone light beam and to focus said hollow-cone light beam at one point of micrometric size in the image focal plane.

According to a particular embodiment, the first conical lens comprises a conical face centred on the optical axis and arranged toward the collimated incident light beam and the second conical lens comprises a conical face centred on the optical axis and arranged toward the first hollow-cone light beam.

Advantageously, according to a particular embodiment, the hollow-cone lighting optical device further comprises an afocal optical system arranged either between illumination means and the first conical lens, or between the first conical lens and the second conical lens, or between the second conical lens and the objective.

According to a particular aspect of this embodiment, the hollow-cone and point-focusing lighting optical device further comprises means for axial displacement of said afocal optical system along the optical axis.

Advantageously, the hollow-cone and point-focusing lighting optical device further comprises means for axial displacement of the first and/or the second conical lens along the optical axis so as to modify the geometric dimensions of the black-background cylindrical light beam.

According to a particular embodiment, the hollow-cone and point-focusing lighting optical device further comprises means for polarisation of the lighting optical beam.

The invention also relates to an optical microscope comprising a hollow-cone and point-focusing lighting optical device according to one of the embodiments described.

The invention also relates to a microspectrometer comprising a hollow-cone and point-focusing lighting optical device according to one of the embodiments described, to light a sample by a hollow-cone light beam focused at one point, so as to generate an optical beam transmitted, reflected or scattered by the sample, said microspectrometer further comprising an optical component able to spatially split said hollow-cone lighting beam and at least one part of the optical beam transmitted, reflected or scattered by the sample so as to form a collected beam and to direct said collected beam toward a spectrometer.

More particularly, the invention relates to a hollow-cone and point-focusing Raman microspectrometer in which said optical component is a collecting mirror inclined with respect to the optical axis so as to collect a Raman back-scattering beam coming from a sample, said mirror being arranged inside the hollow-cone lighting beam.

According to a particular embodiment, the invention relates to a hollow-cone Raman microspectrometer in which said optical component is a mirror inclined with respect to the optical axis so as to receive the black-background cylindrical light beam and to direct it toward the objective, said mirror comprising an opening so as to let through a back-scattering beam coming from a sample and collected by the objective.

According to a particularly advantageous embodiment, the invention proposes a tip-enhanced Raman microspectrometry device comprising a hollow-cone Raman microspectrometer according to one of the embodiments described and a near-field microscope including a tip having an end placed at the focusing point of the hollow-cone light beam.

According to a first variant of the tip-enhanced Raman microspectrometry device, the microscope is a straight microscope, the near-field microscope tip and the hollow-cone and point-focusing lighting optical device being placed on a same side of the sample.

According to another variant of the tip-enhanced Raman microspectrometry device, the microscope is a reversed microscope, the end of the near-field microscope tip being placed opposite the hollow-cone lighting optical device so that the hollow-cone light beam is focused through a transparent sample at the end of the tip.

The invention also relates to a polarimetric microscope comprising a hollow-cone and point-focusing lighting optical device according to one of the embodiments described and further comprising a polarisation state generator and a Cartesian-Cylindrical polarisation converter arranged on the path of the illumination beam and means for collecting a beam scattered by a sample.

The invention also relates to a microellipsometer comprising a hollow-cone and point-focusing lighting optical device according to one of the embodiments described and further comprising means for modulating the polarisation state of the hollow-cone and point-focusing light beam and means for analysing the polarisation state of the light beam reflected or transmitted by a sample.

The invention also relates to a method of hollow-cone conoscopic lighting in optical microscopy, comprising the following steps:
  receiving a collimated incident light beam on a first conical lens to form a conical light beam having, in a plane transverse to the beam axis, a light distribution comprising a dark central part and a bright ring part,
  receiving said conical light beam on a second conical lens to form a black-background cylindrical light beam having, in a plane transverse to the beam axis, a light distribution comprising a dark central part and a bright ring part,
  focusing said black-background cylindrical light beam at one point in the image focal plane of an objective.

The invention also relates to a method of microspectrometry comprising the steps of the lighting method described, said lighting method being able to generate an optical beam transmitted, reflected or scattered by the sample and further comprising the following steps:
  collecting at least one part of the optical beam transmitted, reflected or scattered by the sample, and
  transmitting the collected optical beam to a spectrometer.

Finally, the invention relates to the use of a hollow-cone and point-focusing illumination optical device according to one of the embodiments described in a photoluminescence microscope, a fluorescence microscope, a Raman microscope, a SERS or TERS type Raman microscope, a polarimetric microscope, an ellipsometric microscope and/or a Mueller ellipsometric microscope.

The invention will find a particularly advantageous application in Raman microspectrometry and in microellipsometry.

The present invention also relates to the characteristics that will become more apparent from the following description and that will have to be considered in isolation or according to any of their technically possible combinations.

This description, which is given only by way of non-limitative example, will permit to better understand how the invention can be implemented with reference to the appended drawings, in which.

Figure 4A:
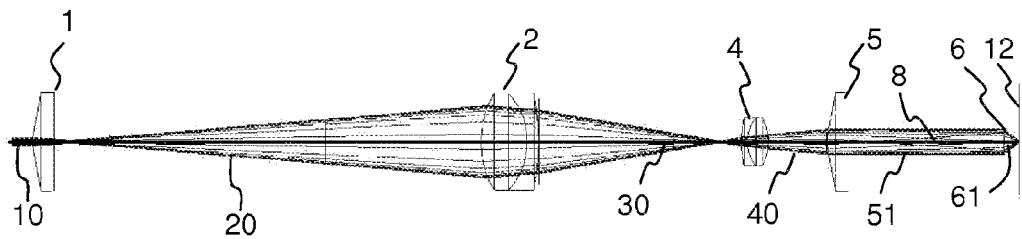
FIG. 4A shows a lighting device according to the second embodiment of the invention and in a first setting position of the lighting optical system, as well as a ray tracing of the illumination beam.
Figure 4B:
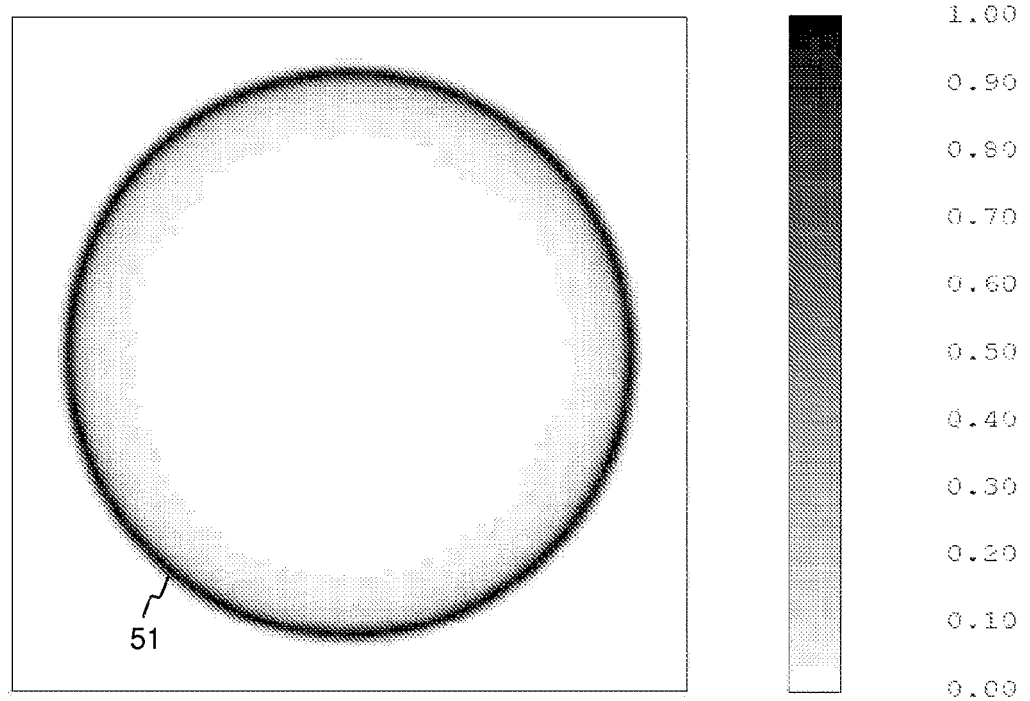
Figure 5A:
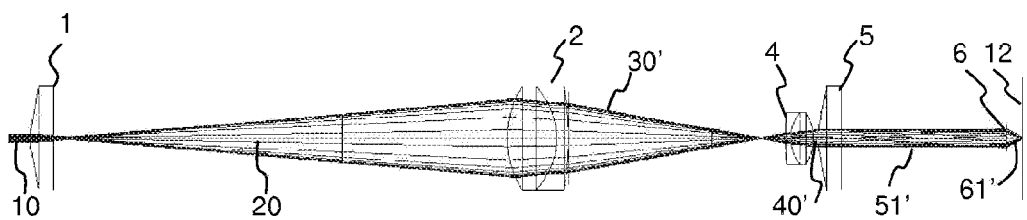
Figure 5B:
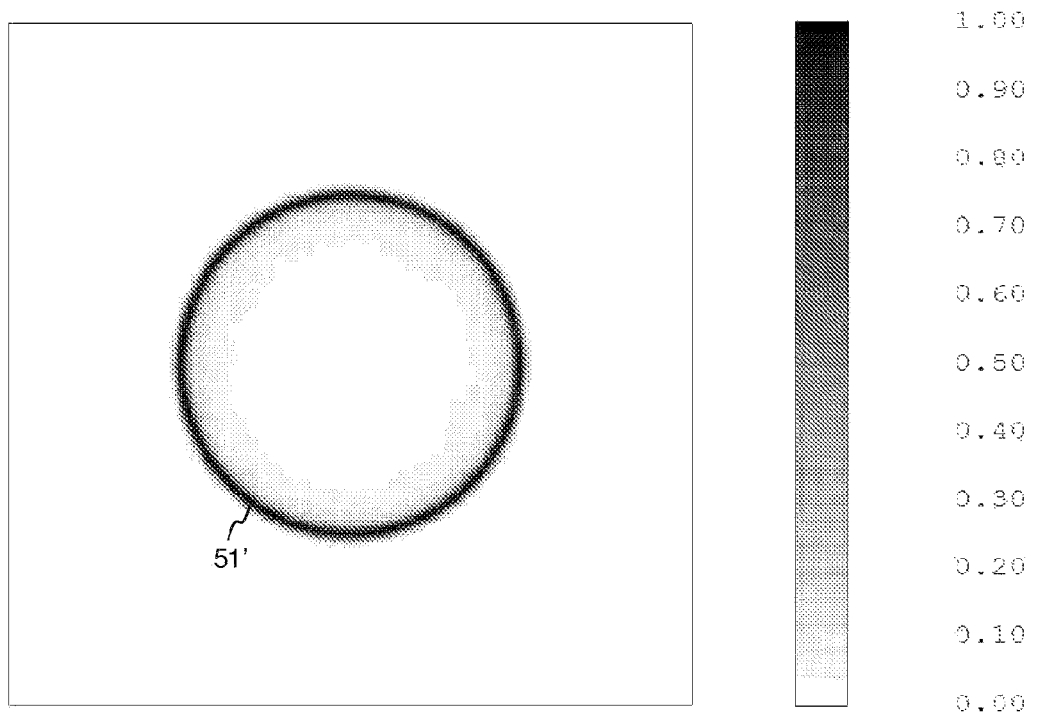
Figure 6:
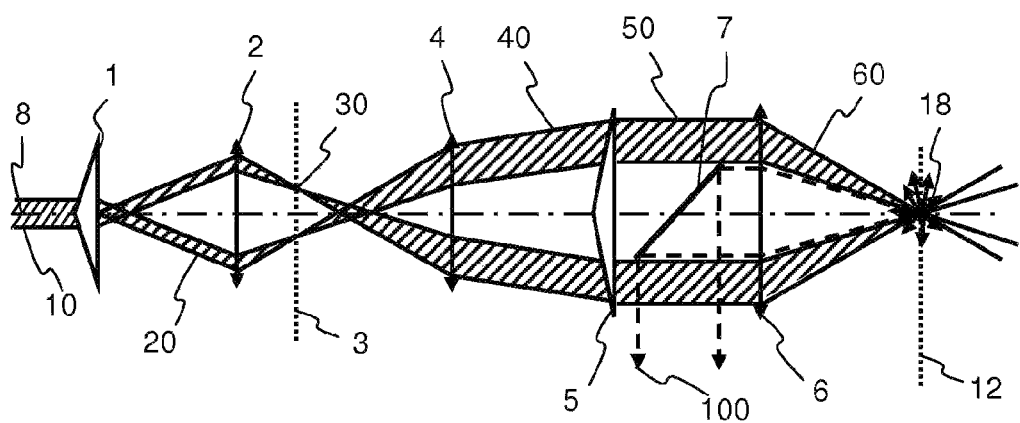
Figures 7A, 7B:
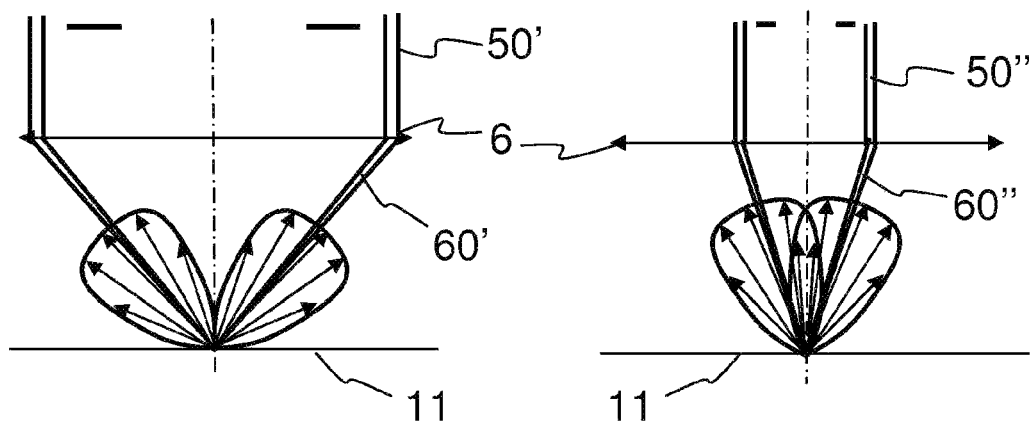
Figure 8:
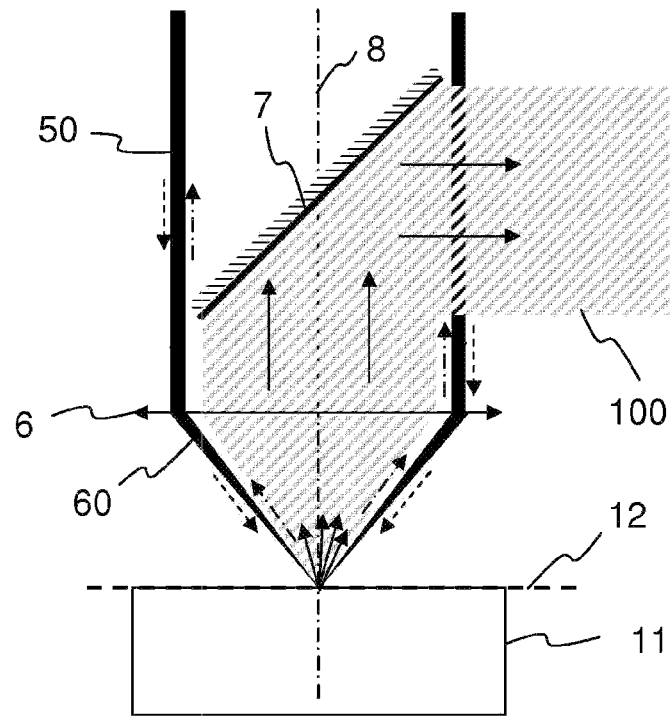
Figure 9:
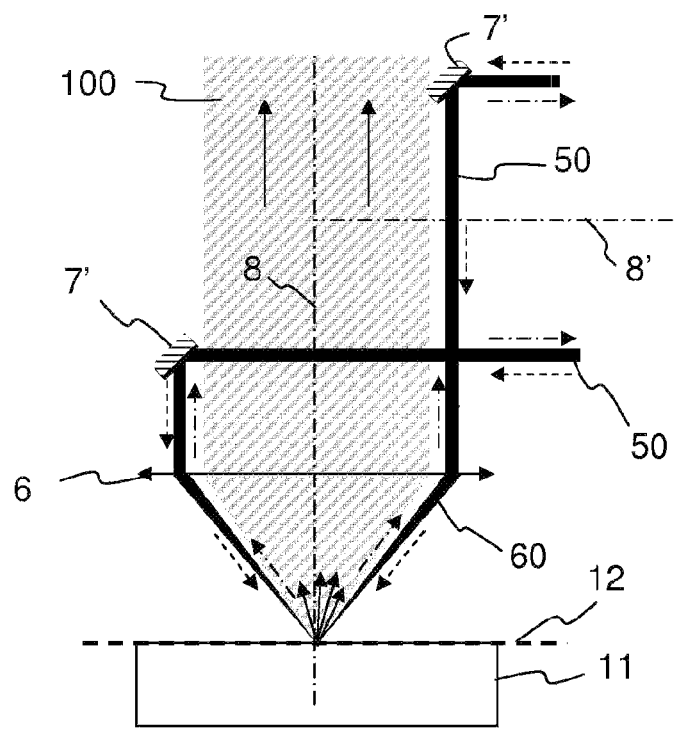
Figure 10A:
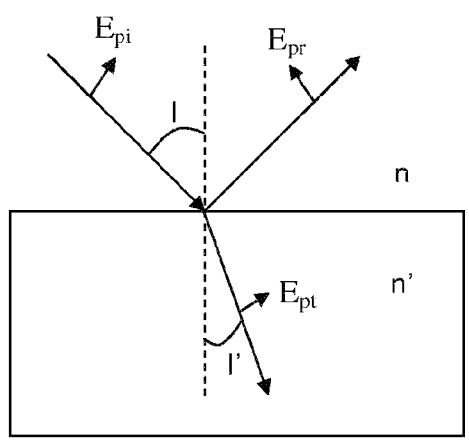
Figure 10B:
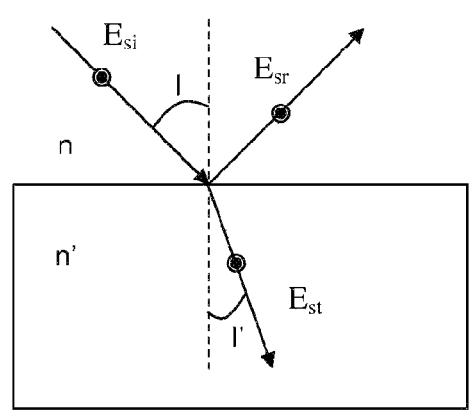
Figure 11:
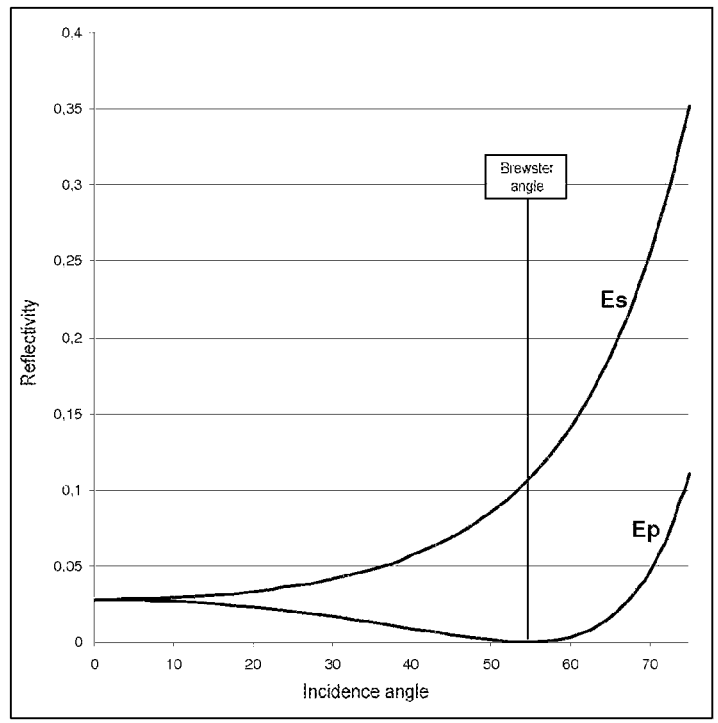
Figure 12:
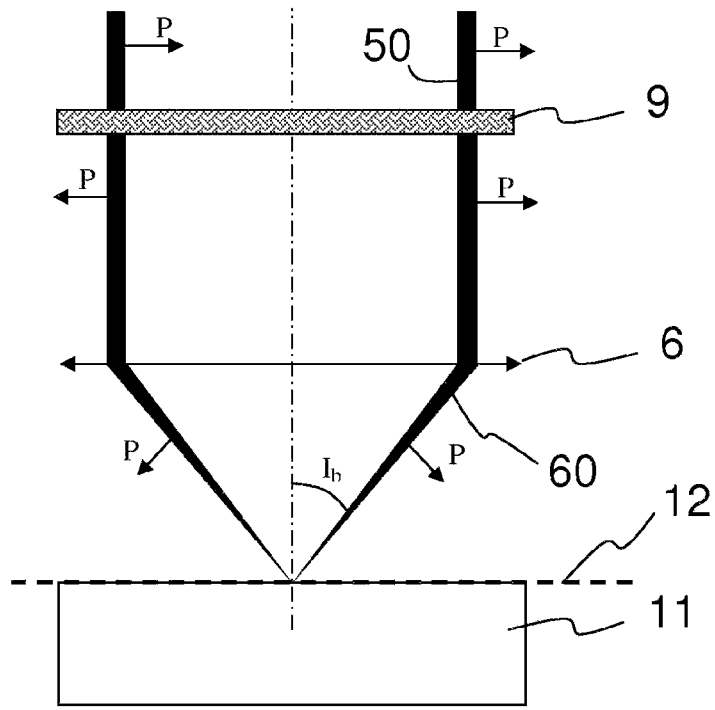
Figure 13:
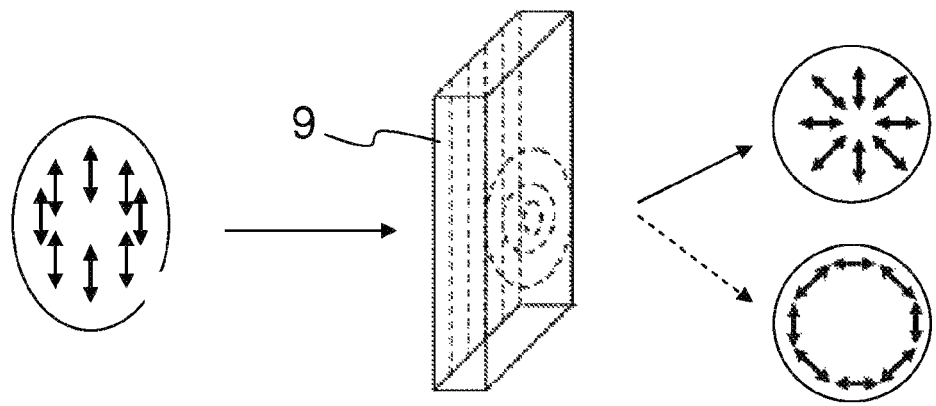
Figure 14:
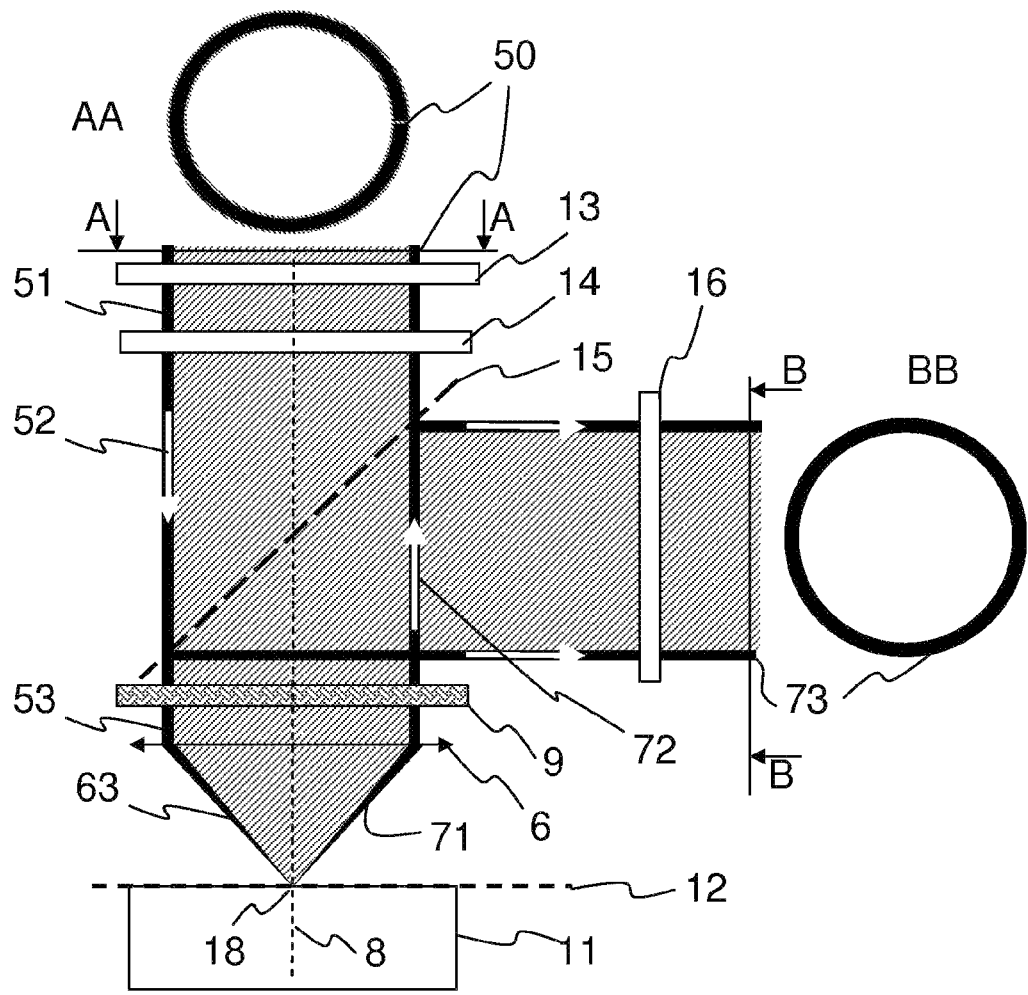
Figure 15:
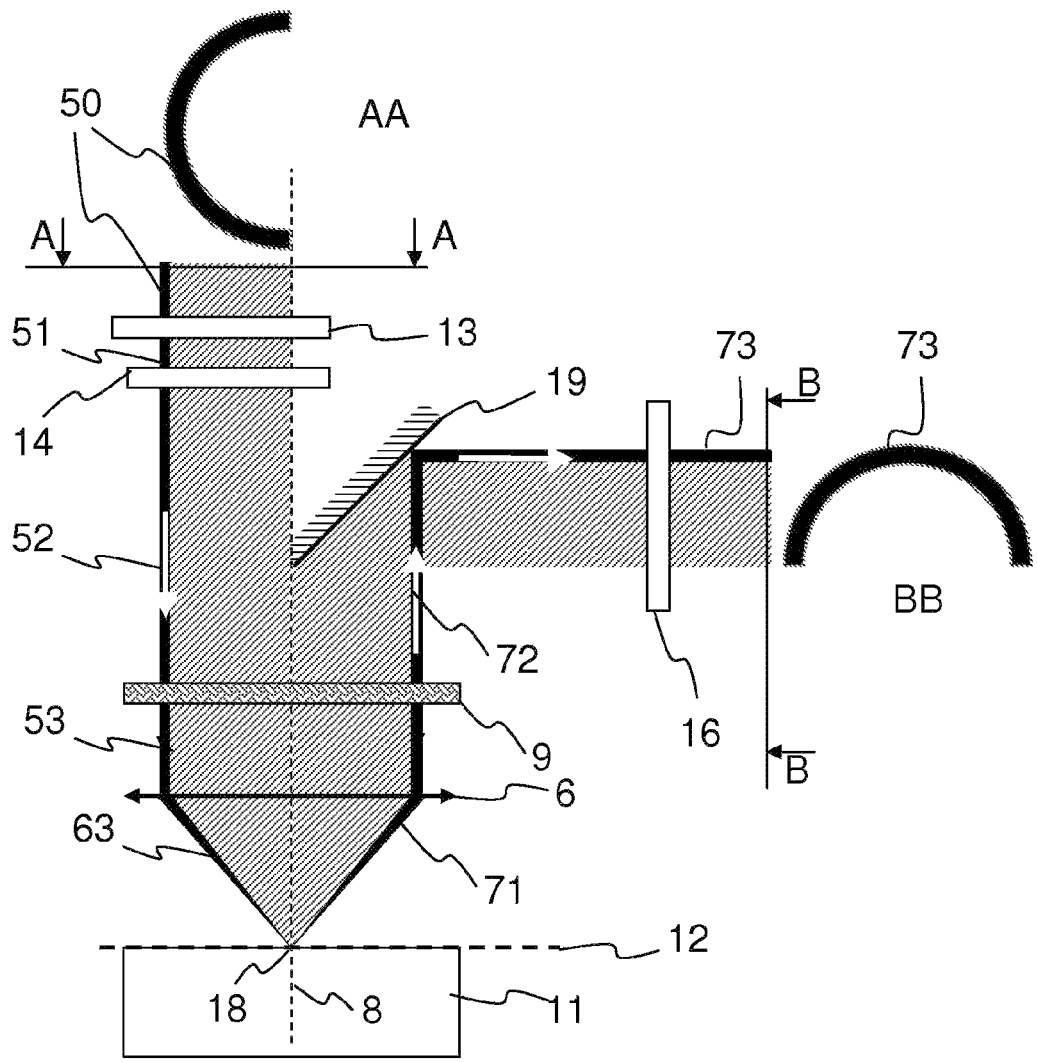
Figure 16A:
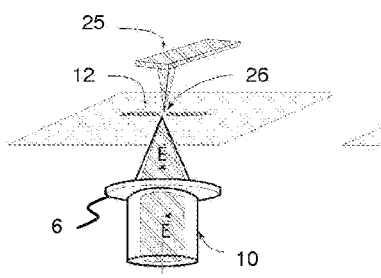
Figure 16B:
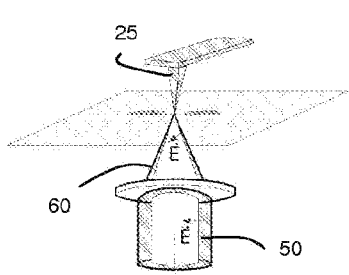
Figure 16C:
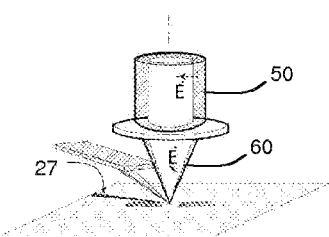

FIG. 4B schematically shows a lighting diagram of the illumination beam of the device of FIG. 4A in a plane transverse to the optical axis;

FIG. 5A shows the lighting device of FIG. 4A in a second setting position of the lighting optical system, as well as a ray tracing of the illumination beam;

FIG. 5B schematically shows a lighting diagram of the illumination beam of the device of FIG. 5A in a plane transverse to the optical axis;

FIG. 6 shows a sectional view of a lighting and beam collecting device according to a preferred embodiment of the invention;

FIGS. 7A-7B schematically show a sectional view of the hollow-cone lighting beam focused at one point on a sample, for different beam sizes, respectively;

FIG. 8 shows a part of a lighting and scattered beam collecting device according to an embodiment of the invention;

FIG. 9 shows a part of a lighting and scattered beam collecting device according to another embodiment of the invention;

FIGS. 10A-10B schematically show the components of the electric field, according to the polarisations p and s, respectively;

FIG. 11 shows a simulation of the reflectance for the polarisation components p and s of the electric field as a function of the incidence angle for a sample;

FIG. 12 shows a part of a hollow-cone polarized lighting device according to a particular embodiment of the invention;

FIG. 13 schematically shows the operation of a Cartesian-cylindrical polarisation converter used in a microellipsometer or a micropolarimeter in a particular embodiment of the invention;

FIG. 14 schematically shows a microellipsometer according to a first embodiment of the invention;

FIG. 15 schematically shows a microellipsometer according to a second embodiment of the invention;

FIG. 16A shows a TERS device according to the prior art, FIG. 16B shows a TERS device coupled to a hollow-cone point lighting device in a reversed microscope, and FIG. 16C shows a TERS device coupled to a hollow-cone point lighting device in a reversed microscope.

The device and the method of the invention are based on the use of a lighting optical system comprising a plurality of axicons and more precisely at least two conical lenses. A conical lens is an optical component generally made of glass, comprising a first conical face and a second face that may be plane, concave spherical or convex spherical. A plano-conical lens may be defined by the half-apex angle $\alpha$ of its conical face. An axicon is an optical component of cylindrical symmetry that images a source point on a focusing line along the optical axis and not at a single focusing point in a single image focal plane. The use of an axicon is known to increase the depth of field of a laser beam. The combination of a conical lens and a spherical lens also allows focusing a collimated beam on a ring.

Figure 1:
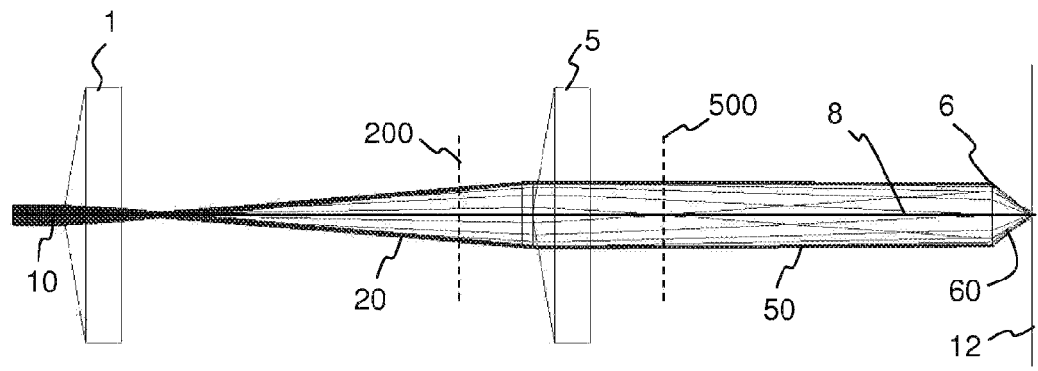
FIG. 1 shows a sectional view of a lighting device according to a first embodiment of the invention and in a first setting position of the lighting beam, as well as a ray tracing of the illumination beam.

FIG. 1 shows a sectional view of a part of a lighting or illumination optical device according to a first embodiment of the invention. The lighting optical device is arranged following the optical axis 8 of a microscope objective 6. In FIG. 1, the incident light beam is shown by the drawing of a few optical rays representative of the aperture of the illumination beam. The lighting device is coupled to a light source (not shown) and to optical means to form a collimated incident beam, and more precisely a bright-background cylindrical incident beam 10. The lighting device comprises a first axicon lens 1, a second axicon lens 5 and an optical objective 6 for focusing the lighting beam in the focusing plane 12 that is a plane transverse to the optical axis 8. The light source has preferably a small geometrical etendue so that the incident beam 10 is as little divergent as possible and so that the image of the source through the lighting device has a micrometric size in the focal plane 12 of the objective 6. In an exemplary embodiment, a laser beam 10 of 2 mm of diameter with a divergence of 1 mrad is used. The device does not include a field diaphragm, because it does not aim to light the whole field of the objective but only one point in the focal plane of the objective. The first axicon lens 1 is preferably centred on the optical axis 8, the conical face of the first axicon lens 1 being preferably placed toward the collimated incident beam 10. The axicon lens 1 deviates the incident beam 10 and forms a divergent conical light beam 20 that is not focused at a focal point. The deviation angle of the conical beam 20 depends on the apex angle and of the refraction index of the material of the first conical lens 1. In a plane 200 transverse to the optical axis 8, the conical beam 20, at the exit of the first conical lens 1, has a dark central area, surrounded by a luminous ring area. However, the conical beam 20 is not focused at one point but at best following a focusing line on the optical axis: indeed, the conical light beam 20 is defined by an inner cone and an outer cone whose respective apexes are not merged at a common point but are spatially split. The second conical lens 5 is in the schema of FIG. 1 centred on the optical axis 8. The conical face of the second conical lens 5 is for example placed toward the conical lighting beam 20. The second conical lens 5 deviates the dark-centre conical beam 20 and forms a black-background cylindrical light beam 50, i.e. a collimated ring light beam 50. In a plane 500 transverse to the optical axis 8, the black-background cylindrical beam 50, at the exit of the second conical lens 5, has a dark central area, surrounded by a luminous ring area, of constant inner and outer diameters whatever the plane 500 transverse to the optical axis 8 between the second conical lens 5 and the objective 6. The objective 6 is for example a microscope objective. The objective 6 receives the black-background cylindrical beam 50 and focuses it at one point in its image focal plane 12. Hence, the illumination optical device forms a point-focused hollow-cone lighting beam 60. The size of the image point of the source depends on the etendue of the source and on the magnification of the lighting system. The geometrical etendue of the source has an influence not only on the size of the spot but also on the "thickness" of the ring of the cylindrical beam 50. That is why we use preferably a collimated laser source or a white source of small geometric etendue. When the lighting optical system is perfectly aligned on the optical axis 8, the lighted point is merged with the focal point of the objective 6. The hollow-cone beam 60 determines the incident angle range of the illumination beam in the focal plane 12, at the focusing point of the beam. This incidence angle range depends in particular on the characteristics of the first conical lens 1 and of the second conical lens 5.

Figure 2:
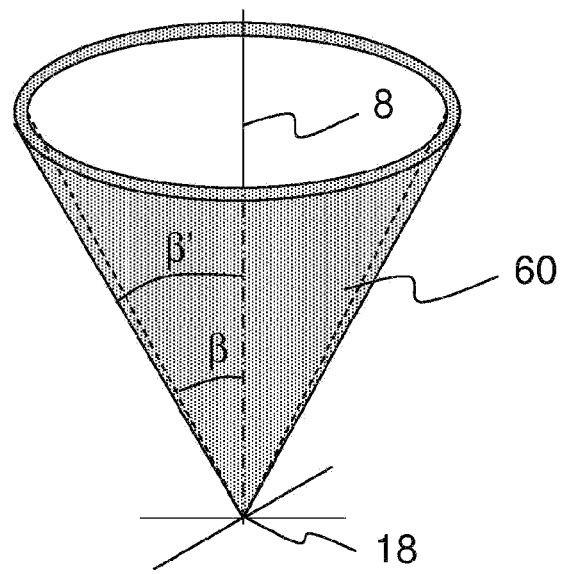
FIG. 2 shows a perspective view of a hollow-cone light beam focused at one point.

FIG. 2 schematically shows a hollow-cone and point-focusing conoscopic light beam 60 obtained by means of the lighting device of FIG. 1. The grey area corresponds to the hollow cone of light and is located between a first cone of apex angle β and a second cone of apex angle β'. The first and second cones are preferably coaxial to each other, with a single and same apex and respective apex angles β and β' different from each other. The focusing point 18 of the light beam 60 is merged with the apex of the two cones. The incidence angle range of the illumination light beam at the point 18 is thus comprised between the angles β and β'.

A simple way to vary the incidence angle range of the hollow-cone lighting beam, without changing an optical component, will now be exposed.

Figure 3:
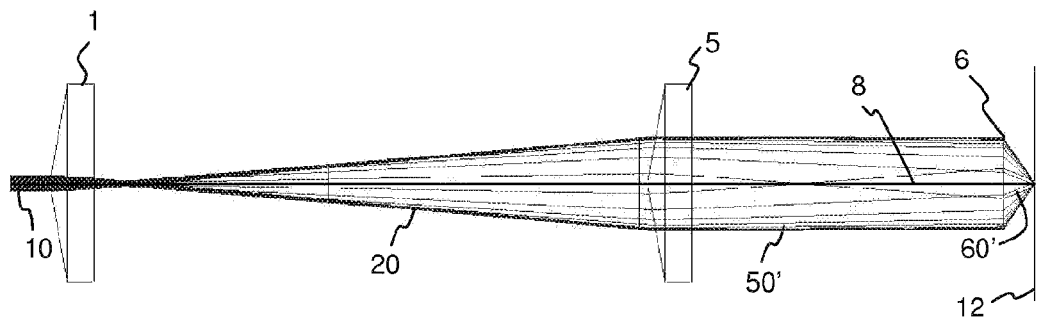
FIG. 3 shows a sectional view of a lighting device according to the first embodiment of the invention, in a second setting position of the lighting beam, as well as a ray tracing of the illumination beam.

FIG. 3 shows a lighting optical device using the same optical components as the device shown in FIG. 1, in particular the same conical lenses 1 and 5. The device of FIG. 3 differs only from that of FIG. 1 by the axial position of the second conical lens 5, the axial position of the first conical lens 1 and of the objective 6 remaining fixed, which allows keeping a fixed focusing plane 12 and a fixed focusing point 18. The device of FIG. 3 comprises for example means for the axial displacement of the second conical lens 5 parallel to the optical axis 8. The aperture of the incident beam 10 is also identical to that of the incident beam of the device of FIG. 1. The operation of the device of FIG. 3 is identical to that of FIG. 1. However, the second conical lens 5 being far from the first conical lens 1, the second conical lens 5 intercepts the conical light beam 20 in a plane where its diameter is greater than in the axial setting of FIG. 1. The second conical lens 5 therefore forms a black-background cylindrical light beam 50', or a collimated ring light beam 50' of diameter higher than the diameter of the black-background cylindrical light beam 50 of FIG. 1. Consequently, the objective 6 forms a hollow conical beam 60' having a incidence angle range higher that the incidence angle range of the hollow conical beam 60 of FIG. 1. The axial displacement of the second conical lens 5 leads to a modification of the diameter of the dark-background cylindrical beam 50'. A hollow conical lighting device, having a variable incidence angle while keeping a fixed focusing point, is thus obtained by simple axial displacement of the second conical lens 5.

FIG. 4A shows a lighting device according to a second embodiment of the invention and in a first setting position of the lighting optical system, as well as a simulation of light ray tracing of the illumination beam propagating in the lighting device. In this second embodiment, the lighting device comprises two axicon lenses 1 and 5, as well as an afocal optical system with two spherical lenses 2 and 4 and means for the axial displacement of the afocal system parallel to the optical axis 8. More precisely, the lighting optical device comprises a first conical lens 1 centred on the optical axis 8. The conical lens 1 deviates the incident beam 10 and forms hollow conical light beam 20 that is not focused at a focal point. In a plane transverse to the optical axis 8, the conical beam 20, at the exit of the first conical lens 1, has a dark central area, surrounded by a luminous ring area. However, the conical beam 20 is not focused at one point but at best following a focusing line on the optical axis. The lighting device shown in FIG. 4A also comprises an afocal optical system formed of two spherical lenses, the image focal plane of the first spherical lens 2 being merged with the object focal plane of the second spherical lens 4. The first spherical lens 2 receives the conical beam 20 of the first conical lens 1. The first spherical lens 2 forms a focused light beam 30 in the image focal plane of the first spherical lens 2, in the form of a ring lighting with a dark centre. The second spherical lens 4 receives the ring lighting beam 30 and forms a conical beam 40 not focused at one point but, like the beam 20, following an axial focusing line. In a plane transverse to the optical axis 8, the conical beam 40, at the exit of the second spherical lens 4, has a dark central area, surrounded by a luminous ring area. The afocal optical system formed by the two spherical lenses 2, 4 thus allows increasing, or respectively reducing, the size of the conical beam, while reducing, or respectively increasing, the aperture thereof. The lighting device of FIG. 4A comprises a second conical lens 5 centred on the optical axis 8. The second conical lens 5 deviates the dark-centre conical beam 40 and forms a black-background cylindrical light beam 51, i.e. a collimated ring light beam 51. In a plane transverse to the optical axis 8, the black-background cylindrical beam 51, at the exit of the second conical lens 5, has a dark central area, surrounded by a luminous ring area, of constant inner and outer diameters whatever the transverse plane. The lighting device of FIG. 4A also comprises an optical objective 6 that is for example a microscope objective. The optical objective 6 receives the black-background cylindrical beam 51 and focuses it in its image focal plane 12. That way, a hollow-cone illumination beam 61 focused at one point is obtained in the focal plane of the objective 6. When the lighting optical system is perfectly aligned on the optical axis, the lighted point is the focal point of the objective 6.

FIG. 4B shows the lighting diagram of the device of FIG. 4A at the exit of the second conical lens 5, in a plane transverse to the optical axis 8, i.e. the lighting diagram of the beam 51. The black part in FIG. 4B corresponds to a maximum lighting and the white part in FIG. 4B corresponds to a zero lighting. It can be observed in FIG. 4B the ring lighting of the beam 51 with a luminous ring and a dark centre. In the example of simulation of FIG. 4B, the outer diameter of the dark-centre cylindrical beam 51 is of 6.4 mm. The objective 6 is herein a ×40 microscope objective. The beam focused on the sample 11 has an incidence angle of about 52 degrees.

FIG. 5A shows the same embodiment as the lighting device of FIG. 4A, for another axial position of the afocal system, with a simulation of ray tracing. Compared to the device of FIG. 4A, the afocal system is brought at a few mm from the second conical lens 5. Similarly to the device of FIG. 4A, the lighting device of FIG. 5A generates a dark-background cylindrical lighting beam 51'. However, the axial displacement of the afocal system leads to a modification of the diameter of the black-background cylindrical beam 51', and consequently a modification of the incidence angle of the hollow-cone light beam 61' focused at the focal point of the objective 6.

FIG. 5B shows the lighting diagram of the device of FIG. 5A at the exit of the second conical lens 5, in a plane transverse to the optical axis 8, i.e. the lighting diagram of the beam 51'. In FIG. 5B, the lighting diagram has a luminous ring (shown in black) and a dark centre (shown in white). In FIG. 5B, the diameter of the ring of the light beam 51' is of 3.9 mm. With the same ×40 microscope objective 6, a beam is obtained, which is focused at the point 18 in the focal plane 12 of the objective 6 under an incidence angle of about 38 degrees.

It is observed that a variation of the diameter of the black-background cylindrical light beam 50, 51, 51' translates into a variation of the incidence angle of the lighting beam 60 on the sample 11. The lighting device shown in FIGS. 4A and 5A thus allows obtaining a dark-background and variable-incidence angle lighting beam by displacement of the second conical lens 5. The continuous variation of the incidence angle of the lighting beam 60 may thus be obtained without changing any optical component of the lighting device and without changing the focusing point of the lighting beam 60. On the other hand, the axial displacement of the afocal system with spherical lenses 2, 4 allows varying the thickness of the luminous "tube" of the lighting beam 51, 51'. In FIGS. 4A and 5A, the afocal system is shown on the optical path between the first axicon lens 1 and the second axicon lens 5. However, in other embodiments, the afocal system could be placed upstream from the first conical lens 1 or downstream from the second conical lens 5.

The lighting device illustrated in FIGS. 1, 3, 4A or 5A thus allows obtaining a hollow-cone lighting beam focused at one point and of variable incidence angle. Moreover, this lighting device does not use a central shutter, which allows keeping the major part of the intensity of the incident light beam up to the focusing point 18.

The use of means for axial displacement of the afocal system and means for axial displacement of the second axicon lens allows varying not only the incidence angle of the point-focused hollow-cone beam 60, 61, 61', but also varying the angular range β-β' of the hollow-cone point illumination beam according to the applications.

In an exemplary embodiment, a laser source and a microscope objective of magnification ×50 and numerical aperture equal to 0.95 are used. The pupil diameter is estimated at about 8 mm. The device allows varying the diameter of the laser "tube" from about 4 mm to 8 mm, i.e. an incidence angle variation at the focusing point comprised between about 30 degrees and more than 70 degrees with the objective 50×/0.95. The angular width (i.e. the difference β'-β) of the hollow-cone and point-focusing beam varies respectively from 2 degrees to less than 5 degrees as a function of the incidence angle. The spot at the focusing point 18 is of micrometric size.

FIG. 6 schematically shows a sample lighting and back-scattered optical signal collecting device according to a preferred embodiment of the invention. The transmission lighting optical device is arranged following an optical axis 8. As explained above in relation with FIG. 1, 3, 4A or 5A, the lighting device transforms the bright-background cylindrical incident beam 10 into a dark-background cylindrical lighting beam 50, and focuses it into a hollow-cone beam 60 at one point 18. The device comprises a first conical lens 1, a second conical lens 5, an objective 6 and an afocal system comprising a first spherical 2 and a second spherical lens 4, the image focal plane 3 of the first spherical lens being merged with the object focal plane of the second spherical lens 4. A sample to be analysed is preferably placed in the focal plane 12 of the objective 6. In FIG. 6, the volume of the illumination light beam is schematically shown by hatching. The lighting optical device receives a collimated light beam 10 coming, for example, from a laser source (not shown). The same reference signs indicate the same elements in FIG. 6 and in FIGS. 1 to 5. The device of FIG. 6 allows focusing a hollow-cone illumination light beam 60 at one point 18 in the image focal plane of the objective 6.

FIG. 6 also shows an optical device for collecting the light 100 back-scattered in a cone about the optical axis of the lighting beam 60. The optical device for collecting the scattered signal, for example of Raman scattering, comprises a mirror 7 placed between the objective 6 and the second conical lens 5. The mirror 7 is for example a planar mirror. Alternatively, the mirror 7 may be a spherical or aspherical mirror intended to focus directly the collected beam 100 on a spectrometer. The collecting mirror 7 has an outer diameter lower than the inner diameter of the black-background cylindrical light beam 50 so as not to shut the lighting beam. The collecting mirror 7 receives a light beam 100 back-scattered about the optical axis 8 in the dark cone of the lighting beam 50 and deviates it in a direction transverse to the optical axis 8. In other embodiments, the collecting mirror 7 may be located between the sample 11 and the objective 6, in the cone of shade of the lighting beam 60, or also between the afocal optical system and the second conical lens 5, in the cone of shade of the conical beam 40. However, the inside of the cylindrical beam 60 corresponds to the place where the dark area is the more extended, it is therefore more easy to insert therein a return mirror 7.

In a preferred application, the lighting device of FIG. 6 is used to focus an exciting laser beam on a sample 11 and the collecting device serves to collect a Raman back-scattered signal. The collected beam 100 may then be filtered and focused at the entry slit of a Raman spectrometer. As can be seen in FIG. 6, the collecting mirror 7 is located in the dark central cylinder of the lighting beam 50. Therefore, the collecting mirror 7 receives almost no light by reflection of the lighting laser beam on the sample 11. Indeed, on a planar sample 11, the reflected beam is redirected in the lighting cone.

The dark-background lighting and collecting device shown in FIG. 6 collects a back-scattering beam that, by construction, comprises very little reflection of the lighting beam. It is therefore not necessary to filter the collected beam to split it from the lighting beam, it is just necessary to filter the Rayleigh scattering. It is then possible to perform Raman spectrometry measurements using a rejecting filter having mean rejection properties (for example, a density of 4 instead of 6), since it is just necessary to spectrally filter the collected beam 100 to split the Raman scattering from the Rayleigh scattering, at the laser wavelength. The lighting and collecting device of FIG. 1 also allows obtaining more easily low-frequency Raman signals, i.e. close to the lighting laser wavelength, without requiring the use of a rejection filter with a low spectral band and a high rejection rate (for example 10 $cm^{-1}$ instead of 50 $cm^{-1}$), as the notch filters used until now for the low-frequency Raman spectrometry applications.

The hollow-cone and variable-incidence angle point lighting device allows new applications, for example in Raman microspectrometry. FIG. 7A schematically shows a first configuration of a hollow-cone point lighting device, in which the outer diameter of the black-background cylindrical light beam 50' corresponds to almost the maximal aperture of the objective 6. The light beam 60' lights the sample 11 under a mean incidence angle corresponding to the numerical aperture of the objective 6. The incidence angle of the lighting beam 60' is for example of 52 degrees, as described in relation with FIG. 4A. FIG. 7B schematically shows a second configuration of the hollow-cone point lighting device, in which the outer diameter of the black-background cylindrical light beam 50" corresponds to almost half of the maximal aperture of the objective 6. Consequently, the light beam 60" lights the sample 11 under a mean incidence angle corresponding to half the numerical aperture of the objective 6. The incidence angle of the lighting beam 60" is for example of 38 degrees, as described in relation with FIG. 5A. In FIGS. 7A and 7B, the arrows schematically represent the scattering pattern of the sample subjected to a hollow-one point light beam. The envelope of the scattering pattern is schematically represented by a curve surrounding the scattering arrows. The incidence angle variation of the lighting beam may then be used to probe a sample under various incidence angles. Raman microspectrometry under variable incidence may be function of the properties of the sample 11, as for example its surface roughness. The lighting device of the invention thus offers news applications of Raman microspectrometry under variable incidence angle, which may provide information that was inaccessible until now on the samples to be analysed. Indeed, in the prior art, Raman microspectrometry does not provide angular resolution as a function of the incidence angle.

FIG. 8 schematically shows a part of a lighting and scattering-signal collecting device according to an embodiment similar to that detailed in relation with FIG. 6. FIG. 8 shows more precisely the black-background cylindrical light beam 50 focused by the optical objective 6 on the sample 11 at one point in the image focal plane of the objective 6. The optical path of the illumination light beam 50, 60 is represented in FIG. 8 in thick black line. The dashed arrows schematically represent the direction of propagation of the lighting beam at the laser wavelength. The dash-dot arrows schematically represent the direction of propagation of the beam specularly reflected by the sample 11 at the laser wavelength. The full-line arrows schematically show the direction of propagation of the beam scattered by the sample 11, collected by the mirror 7 and deviated in a transverse direction, for example toward a spectrometer. The scattered beam comprises a Rayleigh scattering part and a Raman scattering part. The collected scattered beam 100 is represented in FIG. 8 by a hatched area. It can be observed in FIG. 8 that the specular reflection on the sample is superimposed to the dark-centre cylindrical lighting beam, but does not extend in the dark cone. Therefore, the collecting mirror 7 receives only a beam 100 coming from the scattering on the sample. The lighting and collecting device shown in FIG. 8 thus performs, by construction, a very efficient filtering of the light reflected at the laser wavelength. Now, the intensity of the reflected signal at the laser wavelength is generally far higher than the intensity of the Rayleigh scattering beam and the Raman scattering beam. To extract the Raman signal from the collected scattering beam 100, it is not necessary to filter the laser beam reflected on the sample, but only the Rayleigh scattering. Thanks to the lighting and collecting device of the invention, the filtering of the collected beam 100 is easier. A filter having a mean rejection rate (cf. hereinabove) may be sufficient to obtain Raman spectrometry measurements. On the other hand, the lighting and collecting device may advantageously be used for low-frequency Raman spectrometry measurements.

FIG. 9 schematically shows a part of a lighting and signal collecting device according to a second embodiment of the invention. Similarly to FIG. 8, the optical path of the illumination light beam 50, 60 is represented in a thick dark line; the collected scattered beam 100 is represented by a hatched area; the dash arrows represent the direction of propagation of the lighting beam at the laser wavelength; the dash-dot arrows represent the direction of propagation of the beam specularly reflected by the sample 11 at the laser wavelength, and the full-line arrows schematically represent the direction of propagation of the beam scattered by the sample 11. The lighting device comprises a first conical lens, an afocal optical system and a second conical lens (not shown), arranged so as to generate a black-background cylindrical light beam 50. The lighting beam propagates in a direction generally transverse to the normal to the sample 11. The lighting device of FIG. 9 further comprises a mirror 7' arranged between the second conical lens 5 and the objective 6. The mirror 7' is inclined with respect to the axis of the black-background cylindrical light beam 50, so as to deviate it toward the focusing objective 6. The objective 6 focuses the hollow-cone light beam 60 at one point of the sample 11, so as to produce a hollow-cone point conical lighting. The scattering beam 100 is generated by scattering on the sample 11. The scattered beam 100 is collected by the objective 6 to be transmitted toward a spectrometer and/or an imaging detector. The mirror 7' is preferably ring or ellipse-shaped and comprises an central opening of sufficient size to let the scattered beam 100 pass through about the normal to the sample 11. The device of FIG. 9 allows collecting the back-scattered signal in the cone of shade of the black-background cylindrical light beam 50. Similarly to the device of FIG. 8, the collected scattered beam 100 is practically free from specular reflection of the lighting beam on the sample 11. The device of FIG. 9 also allows avoiding the use of expensive, high rejection rate, rejecting filters and may allow performing low-frequency Raman spectrometry measurements.

The hollow-cone point lighting beam, for example according to FIGS. 6 to 9, allows contemplating new Raman microspectrometry applications.

A first category of applications relates to the technique called SERS, for Surface Enhanced Raman Scattering, in which particles of noble metals, such as gold or silver, on which molecules to be analysed come and fix, are deposited on a support. The gold layer allows amplifying the Raman signal. The polarisation and the incidence angle of the illumination beam may play an important role in the amplification of the SERS Raman signal. The use of the illumination device of the invention for the SERS analysis may allow an improvement of the SERS technique sensitivity.

Another category of applications relates to the techniques called TERS (Tip Enhanced Raman Scattering), which use the local amplification of the Raman signal of a sample induced near an AFM (Atomic Force Microscope) tip under the influence of a laser beam 26 focused on this AFM tip. The condition to generate a TERS effect is that the electromagnetic field of the laser beam has to be parallel to the AFM tip. Certain systems do not fulfil this condition, for example the reversed microscopes (cf. FIG. 16A) for which the full-cone conical laser beam 10 arrives straight on the sample in the focal plane 12 of the objective 6 and on the AFM tip 25 (perpendicular electromagnetic field). Two solutions are generally implemented to solve this problem: using a radial-polarisation laser beam and large numerical aperture objectives. FIG. 16A schematically shows a reversed microscope coupled to a tip 25 (for example, an AFM tip), the lighting beam 10 being a full laser beam focused in the focal plane 12 of an objective 6. The TERS lighting laser beam is a preferably radial polarisation laser beam and is focused through a transparent sample in the vicinity of the tip 25. In FIG. 16A has been shown in grey the central part of the laser beam and in white the external part of the laser beam. The central part of the laser beam is the more energetic because it concentrates 90% of the energy of the laser beam, whereas the external part of the conventional laser beam corresponds to less than 10% of the energy. Those techniques allow generating an electromagnetic field parallel to the AFM tip, but only for the external rays of the laser beam, the farthest from the optical axis. Indeed, as indicated in FIG. 16A, the internal part of the laser beam does not contribute to the TERS exaltation because the electromagnetic field here is not parallel to the tip. Moreover, this type of beam (such as in FIG. 16A) generates a warming of the sample and of the tip, that can lead to the destruction thereof. FIGS. 16B and 16C represent a tipped microscope 25 coupled to a hollow-cone point illumination device. In FIG. 16B, the microscope is reversed, and in FIG. 16C the microscope is straight. Advantageously, in the case of a reversed microscope as shown in FIG. 16B, the tip is arranged opposite the hollow-cone point illumination device, the tip being on one side of the sample, and the hollow-cone point illumination device generates a hollow-cone light beam focused through the transparent sample on the end of the tip 25. Preferentially, in the case of a reversed microscope, the axis of the tip 25 is aligned with the optical axis of the conical light beam 60. Advantageously, in the case of a straight microscope as shown in FIG. 16C, the tip and the hollow-cone point illumination device are arranged on the same side of the sample and the hollow-cone point illumination device generates a hollow-cone light beam focused in the plane of the sample on the end of the tip 25. Preferentially, in the case of a straight microscope, the axis of the tip 25 is located outside the lighting cone of the conical light beam 60. In FIGS. 16B and 16C, the grey part of the beam 50, 60 corresponds to the most energetic part of the hollow-cone laser beam, whereas the white central part corresponds to an almost-zero lighting. The hollow-cone point illumination system of the invention applies very advantageously to the TERS techniques. Indeed, the hollow-cone illumination system (as shown in FIGS. 16B and 16C) redistributes the major part of the central energy of the laser beam in a hollow cone (beam 50, 60) and avoids a lighting on the axis of the laser beam. The components of the electromagnetic field vector of the laser beam become predominantly parallel to the AFM tip 25: the TERS exaltation is not only present but strongly increased, of the order of 90% (cf. FIG. 16B). Moreover, a same TERS efficiency may then be obtained with a far less intense lighting laser beam, because almost all the useful energy of the beam is used. Another advantage of the hollow-cone system is to reduce the ratio of the TERS amplification to the warming of the sample and of the tip, allowing the use of a less powerful laser beam for a given amplification. In the case of the straight microscope, an interesting aspect of the hollow-cone technique is to free a part of the laser and thus to avoid in great part the shade 27 created by the tip (FIG. 16C).

FIGS. 10 to 15 relates to another application of the polarized-light hollow-cone point lighting device, for example for polarized Raman spectrometry, polarimetry or also ellipsometry. FIGS. 10A and 10B schematically show the components of the electric field of a planar light wave, according to the polarisations p and s, respectively. $E_{pi}$ represents the component of the p-polarized incident electric field, i.e. in the incidence plane of the beam; $E_{pr}$ and $E_{pt}$ represent the reflected and transmitted, respectively, and p-polarized components of the electric field. $E_{si}$, $E_{sr}$ and $E_{st}$ represent the incident, reflected and transmitted, respectively, and s-polarized, i.e. perpendicularly to the incidence plane, components of the electric field. It is known that the reflection coefficient of an optical beam on the surface of a sample depends on the incidence angle and the polarisation state of the incident light beam. If I is the angle of incidence on the sample, and I' the angle of refraction of the transmitted beam, the Descartes formulas (equations I and II hereinafter) give the reflection coefficients for the polarisations p and s, respectively, as a function of the refraction indices of the incident medium (n) and of the transmission medium (n'):

$$r_{es}=(n\times\cos(I)-n'\times\cos(I'))/(n\times\cos(I)+n'\times\cos(I')) \quad (I)$$

$$r_{ep}=(n'\times\cos(I)-n\times\cos(I'))/(n'\times\cos(I)+n\times\cos(I')) \quad (II)$$

Certain materials have a Brewster angle $I_b$ defined by tan $(I_b)=n'/n$. When the light beam is incident under the Brewster angle, $I_b$, only the component of the electric field $E_{rs}$ perpendicular to the incidence plane is reflected. The reflection of the component of the electric field $E_{rp}$ having a polarisation perpendicular to the incidence plane is zeroed at the Brewster angle. FIG. 11 shows the reflectance for the polarisations p and s, respectively, for an incident light beam on a sample. The Brewster angle in such conditions is about 55 degrees.

According to an embodiment of the lighting device of the invention, the hollow-cone illumination beam is focused at one point on the sample under suitable incidence angle and polarisation. This configuration allows reducing considerably the reflection of the lighting beam, for example a laser beam, on the surface of the sample.

FIG. 12 schematically shows a sectional view of a part of a polarized hollow-cone point lighting device according to a third embodiment of the invention. The lighting device comprises, as described above, an optical system comprising a first conical lens, a second conical lens, so as to generate a dark-background cylindrical beam 50, and an objective 6 to focus the dark-background lighting beam 60 at one point in the focal plane 12 of the sample 11, and possibly an afocal optical system based on two spherical lenses. The lighting device of FIG. 12 further comprises a polarisation converter 9 arranged between the second conical lens 5 and the objective 6, i.e. on the optical path of the dark-background cylindrical light beam 50. The cylindrical beam 50 is preferably polarized linearly following the direction p parallel to the plane of the FIG. 12. In FIG. 12, the arrows represent a component of a p-polarized electrical field in the plane of FIG. 12. However, the lighting beam has a symmetry of revolution about the optical axis 8. To obtain the same polarisation state whatever the incidence plane about the optical axis 8, a polarisation converter 9 is used, of the Cartesian-cylindrical type, operable to receive a beam having a spatially uniform polarisation state distribution and to convert it into a beam having a polarisation state distribution with a cylindrical symmetry about the optical axis.

The polarization converter 9 is preferably a spatial polarisation distribution converter, which allows generating a beam with a cylindrical polarisation state distribution, for example radial or azimuthal, marketed by the Arcoptics company for example (or Z-Pol by Microlaser), or also a converter of the generalized cylindrical type (or CV beam). FIG. 13 schematically shows the operation of a radial and azimuthal polarisation converter based on liquid crystals. An incident beam is polarized in a linear and spatially uniform manner. According to the orientation of the entry linear polarisation, which is either parallel or perpendicular to the axis of alignment of the liquid crystals on entry face of the converter 9, a linearly polarized beam, but with either a radial (on the top right in FIG. 13) or azimuthal (on the bottom right in FIG. 13) polarisation distribution is obtained at the exit of the converter. For these two polarisation distributions, radial and azimuthal, respectively, the polarisation state is identical in any incidence plane about the optical axis.

The patent application FR1055839 describes in details the structure and the operation of a generalized Cartesian-cylindrical polarisation distribution converter. Therefore, in each incidence plane about the optical axis, the beam focused on the sample is polarized according to the direction P, parallel to the incidence plane. In each incidence plane about the optical axis, the sample may be lighted under the Brewster angle and with a polarisation state P, whatever the incidence plane. It is then possible to fully zero the reflection of the laser beam in all the incidence planes. Now, as explained hereinabove, in Raman spectrometry, it is very interesting to limit the collection of the laser beam, as it facilitates the filtering (i.e. the dissociation of the Raman beam and of the laser beam). The polarized lighting device of FIG. 12 thus allows improving the filtering performance, for example to carry out Raman spectrometry measurements at a lower frequency, or to use a less performing and thus less expensive filtering device.

Such a lighting device combined with a cylindrical-symmetry polarizing component advantageously applies to a micro-ellipsometer. In ellipsometry, the polarisation state change is determined by the properties of the sample (thickness, refraction index). The study of this polarisation change, and in particular the reflectance ratio for the p- and s-polarized waves allows recovering the two parameters $\text{Tan}(\psi)$ and $\Delta$ (ratio between the two reflection coefficients and phase-shift). By varying the incidence angle and/or the wavelength, and by measuring these two parameters ($\psi$ and $\Delta$), it is possible to recover the properties of the sample (for example thickness and index).

Different methods of "point" ellipsometry exist:
laser ellipsometry has the advantage that it allows obtaining a very small focusing point (high spatial resolution) and a high light intensity (high sensitivity). But laser ellipsometry is monochromatically limited (typically from one to three laser lines), and thus allows obtaining only a limited number of couples $\text{Tan}(\psi)$ and $\Delta$ by measurement (and by the incidence angle);
spectroscopic ellipsometry uses a spectrally wide and continuous or "continuum" source that allows measuring a couple $\text{Tan}(\psi)$ and $\Delta$ for each wavelength in only one time (for an incidence angle) but that does not allow reaching a focusing point as small as with laser ellipsometry (typically 20 µm minimum) and gives no access to a high light intensity.

The lighting device of FIG. 12, coupled to a standard microscope, allows not only to combine the advantages of microscopy and ellipsometry but also to combine the ellipsometric measurement to a conventional optical microscopy analysis, and also a molecular spectroscopy analysis (Raman, fluorescence, PL . . . ).

FIG. 14 schematically shows a sectional view of an ellipsometry device based on the use of a hollow-cone point lighting system and a Cartesian-cylindrical polarisation converter 9. On the top of FIG. 14 is shown a sectional view AA of the tubular incident beam 50 in a plane transverse to the optical axis 8 generated by a system based on conical lenses such as described above. A luminous ring 50 (represented in black in FIG. 13) can be observed. A polarisation state generator 13, which is preferably a linear polarizer, allows generating a beam 51 that is a cylindrical beam polarized linearly following the axis of the polarizer 13 and having a spatially uniform polarisation state distribution. A polarisation modulator allows modulating the polarisation state of the incident beam 52 and performing measurements as a function of the polarisation modulation, for example to extract ellipsometric or Mueller ellipsometry measurements. The polarized beam 52 passes through a splitting plate 14. The Cartesian-cylindrical polarisation converter 9 receives the beam 52 and generates a beam 53 that is polarized following a spatial polarisation distribution of cylindrical symmetry about the optical axis 8. The objective 6 receives the incident beam 52 and forms a cylindrical polarisation-distribution and hollow-cone beam 63, focused at one point 18 in the focal plane 12. The beam 63 is specularly reflected by the sample 11 and comes back on the path of the incident beam provided that the normal to the sample is merged with the optical axis 8 at the point 18. The reflected beam 71 is collected by the objective 6 and passes back through the polarisation converter 9, this time in the cylindrical-Cartesian direction. The beam 72 has a uniform polarisation state distribution. This beam 72 is reflected by the splitting plate 14 toward a polarisation state analyser 16, which is preferably a linear polarizer. Therefore, a hollow-cone cylindrical beam 73 linearly polarized according to the axis of the analyser 16 and having spatially uniform polarisation state distribution in thus obtained at the exit of the device of FIG. 14. The light distribution of the beam 73 is schematically shown according to the section BB. A detector detects the intensity of the beam 73 as a function of the polarisation modulation. The device of FIG. 14 thus allows carrying out ellipsometric measurements ($\psi$, $\Delta$) on a microscopic-size measurement area on the sample, while providing a signal of excellent luminosity, because all the incidence planes about of the optical axis 8 are used. The splitting plate 15 has for effect to attenuate the intensity of the light beam by an attenuation factor equal to about four. The splitting plate 15 may also induce effects on the polarisation requiring an alignment and/or a precise calibration of the optical components of the measurement device of FIG. 14.

FIG. 15 shows a variant of the ellipsometric device of FIG. 14, wherein the splitting plate 15 is replaced by a mirror 19 interposed on a half of the incident beam so as to light over a half-ring 50 and to collect the reflected beam over a half-ring 73. The components similar to those of the device of FIG. 14 are denoted by the same reference signs. The tubular or hollow-cone cylindrical beam 50 is split by means of a mask so as to light over a half-ring, as shown in the section AA. A polarisation state generator 13, preferably a uniform linear polarizer, generates a polarized semi-cylindrical beam 51. A polarisation modulator 14, preferably spatially uniform, modulates the polarisation state of the semi-cylindrical beam 52. A Cartesian-cylindrical (or half-cylindrical) polarisation converter 9 receives the beam 52 and generates a semi-cylindrical beam 53 that is polarized but with a spatial polarisation distribution of cylindrical symmetry with respect to the optical axis 8. The objective 6 receives the semi-cylindrical incident beam 53 and forms a cylindrical polarisation distribution and hollow-cone beam 63 focused at one point 18 in the focal plane 12. The beam 63 is specularly reflected by the sample 11 and forms a reflected beam 71. In the device of FIG. 15, the beam 71 does not come back on the path of the incident beam, but on a half of the cylinder symmetrical with respect to the half-cylinder of the lighting beam 52, when the normal to the sample is merged with the optical axis 8 at the point 18. The objective 6 collects the reflected beam 71 that passes through the polarisation converter 9 in the cylindrical-Cartesian direction. The beam 72 has a uniform polarisation state distribution and a semi-cylindrical intensity distribution. This beam 72 is reflected by a mirror 19 toward a polarisation state analyser 16, which is preferably a linear polarizer. A hollow-cone semi-cylindrical beam 73 linearly polarized following the axis of the analyser 16 and having a spatially uniform polarisation state distribution is thus obtained at the exit of the device of FIG. 15. The light distribution of the beam 73 is schematically shown according to the section BB. A detector detects the intensity of the beam 73 as a function of the polarisation modulation. The masking of half the beam associated to the use of a mirror 19 allows reducing by half the losses of intensity of the signal detected compared to the device of FIG. 14. Moreover, the effects of polarisation of the mirror 19 may be calibrated more easily than those of a splitting plate 14.

It is understood that the hollow-cone point lighting device, for example according to FIGS. 14 and 15, advantageously allows an application to ellipsometry under variable incidence angle.

FIGS. 6-9, 12, 14 and 15 represent lighting and reflected or back-scattered signal collecting devices. The same principles may be applied to a lighting device and a device for collecting a signal transmitted or forward-scattered, i.e. through the sample.

It is particularly advantageous that a same point of a sample can be analysed both by a Raman analysis device and by an ellipsometric analysis device, as exposed in the patent FR2784749. The one skilled in the art will advantageously combine a lighting and scattered signal collecting device according to FIG. 8 or 9 and a lighting and reflected or transmitted signal collecting device according to FIG. 14 or 15 to extract from a same measurement point 18 Raman spectrometry measurements and ellipsometry measurements.

The hollow-cone point illumination device according to one of the embodiments of the invention may be coupled to a standard monochromatic laser source but also to a coherent polychromatic source, as for example a super-continuum source or also a laser-driven plasma source (LDLS source) that allows obtaining a collimated beam of good quality (and spectrally wide), and thus compatible with the device described herein. The device according to the invention allows obtaining a hollow-cone illumination beam without central shutter and thus almost without loss of intensity of the light beam, which is a considerable advantage by comparison with the prior devices.

The hollow-cone point lighting device for a microscope of the invention allows obtaining a better axial resolution (in depth) because it does not produce any laser radiation in the axis outside the focal point, which reduces the depth of field of the lighting beam.

The lighting device allows reducing the influence of the substrate that serves as a support for the sample (no spectral emission of the substrate).

The lighting device allows obtaining a laser light beam with a conical angular distribution.

The device is advantageously adjustable, by axial translation of the second conical lens and/or of an afocal, which allows varying the incidence angle of the lighting beam on the sample, without changing any optical component, and without modification of the focusing point. The incidence angle variation of the dark-background lighting beam allows studying the Raman diffusion "feather", i.e. the distribution of the Raman signal not only in back-scattering configuration following an opposite direction (by 180 degrees) with respect to the incident direction of the lighting beam, but also as a function of other scattering angles.

Outside the focusing plane, the hollow-cone point lighting device of the invention does not collect light from the laser. The filtering of the scattering beam is thus easier, which allows in particular low-frequency Raman measurements, i.e. at wavelengths very close to the wavelength of the excitation laser beam.

The invention claimed is:

1. A hollow-cone and point-focusing conoscopic illumination optical device for an optical microscope, comprising:
   illumination means comprising a point light source, said illumination means being able to generate a collimated incident light beam (10),
   an optical objective (6) having an optical axis (8, 8') and an image focal plane (12), the optical objective (6) being arranged so as to receive a cylindrical incident light beam (50) and to form an image of the source at one point (18) in the image focal point (12),
   characterized in that the illumination optical device comprises:
   an optical system comprising a first conical lens (1) and a second conical lens (5), said optical beam being arranged on the optical path of the incident light beam between the illumination means and the optical objective (6),
   the first conical lens (1) being arranged so as to receive said collimated incident light beam (10) and to form a hollow-cone light beam (20) having, in a plane transverse to the beam axis, a light distribution comprising a dark central part and a bright ring part,
   the second conical lens (5) being arranged so as to receive said first hollow-cone light beam (20, 40) from the first conical lens (1) and to form a black-background cylindrical light beam (50) having, in a plane transverse to the beam axis, a light distribution comprising a dark central part and a bright ring part, and in that the optical objective (6) is arranged so as to receive said black-background cylindrical light beam (50) from the second conical lens (5), to form a hollow-cone light beam (60) and to focus said hollow-cone light beam (60) at one point (18) of micrometric size in the image focal plane (12).

2. The hollow-cone and point-focusing lighting optical device according to claim 1, wherein:

the first conical lens (1) comprises a conical face centered on the optical axis (8) and arranged toward the collimated incident light beam (10); and the second conical lens (5) comprises a conical face centered on the optical axis (8) and arranged toward the first hollow-cone light beam (20, 40).

3. The hollow-cone and point-focusing lighting optical device according to claim 1, further comprising an a focal optical system arranged either between illumination means and the first conical lens (1), or between the first conical lens (1) and the second conical lens (5), or between the second conical lens (5) and the objective (6).

4. The hollow-cone and point-focusing lighting optical device according to claim 1, further comprising means for axial displacement of the first and/or the second conical lens (1, 5) along the optical axis (8, 8') so as to modify the geometric dimensions of the black-background cylindrical light beam (50).

5. The hollow-cone and point-focusing lighting optical device according to claim 1, further comprising means (13, 14, 9) for polarisation of the lighting optical beam.

6. An optical microscope comprising a hollow-cone and point-focusing lighting optical device according to claim 1.

7. A microspectrometer comprising a hollow-cone and point-focusing lighting optical device according to claim 1, able to light a sample (11) by a hollow-cone light beam (60) focused at one point (18) on a sample, so as to generate an optical beam transmitted, reflected or scattered by the sample (11), said microspectrometer further comprising an optical component (7, 7', 15, 19) able to spatially split said hollow-cone lighting beam (40, 50, 60) and at least one part of the optical beam transmitted, reflected or scattered by the sample (11) so as to form a collected beam (100, 71) and to direct said collected beam (100) toward a spectrometer.

8. A hollow-cone and point-focusing Raman microspectrometer according to claim 7, wherein said optical component is a collecting mirror (7) inclined with respect to the optical axis (8) so as to collect a Raman back-scattering beam (100) coming from a sample (11), said mirror (7) being arranged inside the hollow-cone lighting beam (40, 50, 60).

9. A hollow-cone Raman microspectrometer according to claim 8, wherein said optical component is a mirror (7') inclined with respect to the optical axis (4) so as to receive the black-background cylindrical lighting beam (50) and to direct it toward the objective (6), said mirror (7') comprising an opening so as to let through a back-scattering beam (100) coming from a sample (11) and collected by the objective (6).

10. A tip-enhanced Raman microspectrometry device comprising a hollow-cone Raman microspectrometer according to claim 8 and a near-field microscope comprising a tip (25) having an end placed at the focusing point (18) of the hollow-cone light beam (60).

11. The tip-enhanced Raman microspectrometry device according to claim 10, wherein the microscope is a straight microscope, the near-field microscope tip (25) and the hollow-cone and point-focusing lighting optical device being placed on a same side of the sample (11).

12. The tip-enhanced Raman microspectrometry device according to claim 10, wherein the microscope is a reversed microscope, the end of the near-field microscope tip (25) being placed opposite the hollow-cone lighting optical device so that the hollow-cone light beam (60) is focused through a transparent sample (11) at the end of the tip (25).

13. A hollow-cone polarimetric microscope comprising a black-background lighting optical device according to claim 1, and further comprising a polarisation state generator (13, 14) and a Cartesian-Cylindrical polarization converter (9) arranged on the path of the illumination beam between the second conical lens (5) and the objective (6) and means (7, 7') for collecting a beam scattered by a sample (11).

14. A microellipsometer comprising a black-background lighting optical device according to claim 1, and further comprising means (13, 14) for modulating the polarisation state of the hollow-cone and point-focusing light beam (60) and means (16) for analysing the polarisation state of the light beam reflected or transmitted by the sample.

15. A method of hollow-cone conoscopic lighting in optical microscopy, comprising the following steps:

receiving a collimated incident light beam (10) on a first conical lens (1) to form a conical light beam (20) having, in a plane transverse to the beam axis, a light distribution comprising a dark central part and a bright ring part, receiving said conical light beam (20, 40) on a second conical lens (5) to form a black-background cylindrical light beam (50) having, in a plane transverse to the beam axis, a light distribution comprising a dark central part and a bright ring part, and focusing said black-background cylindrical light beam (50) at one point (18) in the image focal plane (12) of an objective (6).

16. The hollow-cone and point-focusing lighting optical device according to claim 2, further comprising an a focal optical system arranged either between illumination means and the first conical lens (1), or between the first conical lens (1) and the second conical lens (5), or between the second conical lens (5) and the objective (6).

17. A hollow-cone and point-focusing conoscopic illumination optical device for an optical microscope, comprising:

an illumination means that generates a collimated incident light beam (10) and comprises a point light source;

an optical objective (6) having an optical axis (8, 8') and an image focal plane (12), the optical objective (6) being arranged so as to receive a cylindrical incident light beam (50) and to form an image of the source at one point (18) in the image focal point (12); and an optical system consisting essentially of a first conical lens (1) and a second conical lens (5), said optical beam being arranged on the optical path of the incident light beam between the illumination means and the optical objective (6), the first conical lens (1) being arranged so as to receive said collimated incident light beam (10) and to form a hollow-cone light beam (20) having, in a plane transverse to the beam axis, a light distribution comprising a dark central part and a bright ring part, the second conical lens (5) being arranged so as to receive said first hollow-cone light beam (20, 40) from the first conical lens (1) and to form a black-background cylindrical light beam (50) having, in a plane transverse to the beam axis, a light distribution comprising a dark central part and a bright ring part, and the optical objective (6) being arranged so as to receive said black-background cylindrical light beam (50) from the second conical lens (5), to form a hollow-cone light beam (60) and to focus said hollow-cone light beam (60) at one point (18) of micrometric size in the image focal plane (12) on a sample,
wherein the first conical lens (1) and the second conical lens (5) each comprise a conical face centered on the optical axis (8) of the optical objective (6) which focuses said hollow-cone light beam on the sample.

\* \* \* \* \*